United States Patent [19]

Treille et al.

[11] 4,113,596

[45] Sep. 12, 1978

[54] METHOD OF MEASURING THE MOBILITY OF COLLOIDS IN AN ELECTRICAL FIELD

[75] Inventors: Pierre Albert Eugéne Treille, Saint Cloud; Jacques Claude Antoine Moles, Nanterre; Maurice Gabriel Ernst Bonnemay, Boulogne; Jean Paul Royon, La Varenne-St. Hilaire; Michel Marc Levart, Issay-les-Moulineaux; Henri Pierre Gaessler, Aubervilliers; Yves Robert Richard, Marly-le-Roi, all of France

[73] Assignee: Degremont, Rueil-Malmaison, France

[21] Appl. No.: 605,926

[22] Filed: Aug. 19, 1975

[30] Foreign Application Priority Data

Sep. 6, 1974 [FR] France .................. 74 30259

[51] Int. Cl.² ............... G01N 27/26; G01N 27/28
[52] U.S. Cl. ............... 204/180 R; 204/299 R; 210/42 R; 356/103
[58] Field of Search ........... 204/180 R, 299, 195 L, 204/292, 280; 356/102, 103, 105; 210/42 R

[56] References Cited

U.S. PATENT DOCUMENTS

| 2,749,293 | 6/1956 | Wahlin | 204/292 X |
| 3,346,4.. | 10/1967 | Widemann | 204/299 |
| 3,454,487 | 7/1969 | Riddick | 204/299 |
| 3,764,512 | 10/1973 | Greenwood et al. | 204/299 |
| 3,783,117 | 1/1974 | Bean | 204/180 R |
| 3,909,380 | 9/1975 | Day et al. | 204/180 R |

OTHER PUBLICATIONS

Willard et al., "Instrumental Methods of Analysis", D. van Nostrand Co., Inc., pp. 20, 22 & 23, (1951).

*Primary Examiner*—Arthur C. Prescott
*Attorney, Agent, or Firm*—Wenderoth, Lind & Ponack

[57] ABSTRACT

The invention relates to a method for the measurement of the movement of colloidal particles in suspensions or solutions. The apparatus used in this method comprises an electrophoresis tank equipped with two electrodes between which an electrical field can be applied.

A beam of radiation produced at the outside of the tank having a thickness of not more than $1000\mu$ as viewed in the direction of the lines of force of the electrical field set up between the electrodes is directed so as to skim the electrode away from which the particles move under the effect of the electrical field.

In order to determine the mobility of the particles the optical density of the liquid is measured a first time without applying the electrical field, and a second time after having applied the field during not more than 10 seconds.

12 Claims, 2 Drawing Figures

METHOD OF MEASURING THE MOBILITY OF COLLOIDS IN AN ELECTRICAL FIELD

BACKGROUND OF THE INVENTION

This invention relates to a method for the measurement of the movement of colloidal particles in suspension or in solution, particularly for the treatment of water in order to determine the optimum dose of coagulant necessary for clarification or for regulating the addition of coagulant.

At the present time, such measurements are carried out using equipment possessing a certain number of disadvantages.

Within the framework of the treatment of water or effluent for example, a very simple method is applied, which consists of carrying out a coagulation test by reproducing te operating conditions of a clarifier. This method makes use of a primitive plant and requires large quantities of water, and in addition, it takes a long time and is not very accurate.

Another and more developed method consists of measuring the charge of the colloidal particles by the addition of an excess of polyelectrolytes and return colorimetric titration of this excess, this titration possessing the disadvantage of being very difficult to carry out.

In addition, installations exist which measure the movement of the colloidal particles in an electrical field.

It is well-known that the stability of colloidal suspensions or solutions is intimately associated with the value, in the receiving medium, of the electrokinetic potential of the particles encountered.

The value of this electrokinetic potential is expressed notably by the movement of the particles in an electrical field. Under these conditions, the measurement of this movement is a means of determining the electrokinetic potential, and therefore of studying the destabilisation by coagulation of colloidal solutions. This movement is well-known under the name of electrophoresis.

The known apparatus for the measuring of electrophoresis is composed of three parts, i.e. two compartments each containing an electrode, connected to each other by a tube which may have a length of approximately 10 cm and a diameter of approximately 4.5 mm. An electrical field of the order of 30 V/cm is created by the application of voltages ranging from 200 to 300 V direct current.

By means of local illumination using an incandescent lamp, the movement of the colloids in the tube is measured optically, using binoculars, one of the oculars of which comprise a micrometer, or again illumination is carried out using a laser, the movement of the colloids being then followed automatically.

All these known installations possess certain inherent disadvantages:

They necessitate the use of statistical measurements. In effect, the distribution of the colloids observed in a liquid is not homogeneous. Certain particles move rapidly, and others move slowly and thus do not react in the same way to a coagulating action. Therefore the individual mobility of each particle is measured.

They are difficult to handle.

They are expensive.

SUMMARY OF THE INVENTION

A method has now been found for the measuring of the mobility of colloidal particles in which a solution or suspension containing colloidal particles is placed in an electrophoresis tank equipped with two substantially parallel electrodes preferably of palladium. A very flat beam of radiation traverses the tank and is directed at a very small distance from one of the electrodes. The value of the optical density of the particles is determined by measuring the intensity of the beam emerging from the tank. An electrical field is applied between the electrodes, and after a brief period of time the value of the optical density is again read. The beam of radiation has a thickness between 0 and $1000\mu$, preferably between 0 and $500\mu$, as viewed in the direction of the lines of force of the electrical field. The beam is directed at a very small distance from the electrode away from which the particles move under the effect of the electrical field, i.e. the active electrode. The variation of the measured optical density is a measure of the mobility of the colloidal particles in the electrical field.

BRIEF DESCRIPTION OF THE DRAWINGS

In the attached drawings, which show diagrammatically and purely as a non-limiting example an emmbodiment of an apparatus for carrying out the invention.

DETAILED DESCRIPTION OF THE INVENTION

Figure 1:
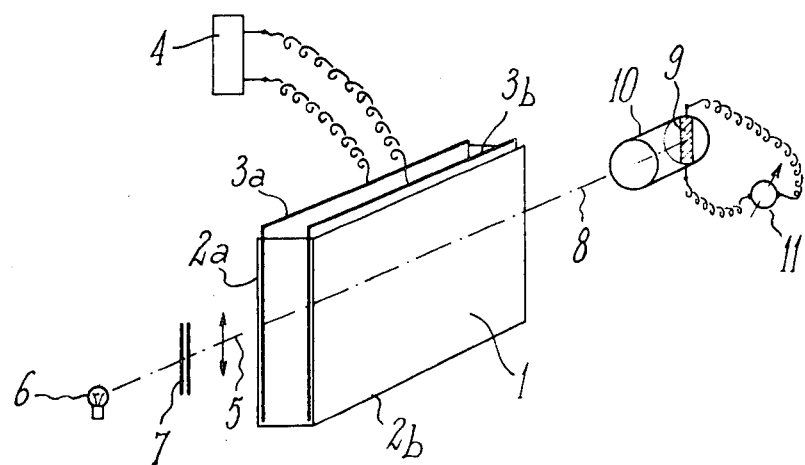
FIG. 1 shows the entire assembly of the devices constituting the apparatus.
Figure 2:
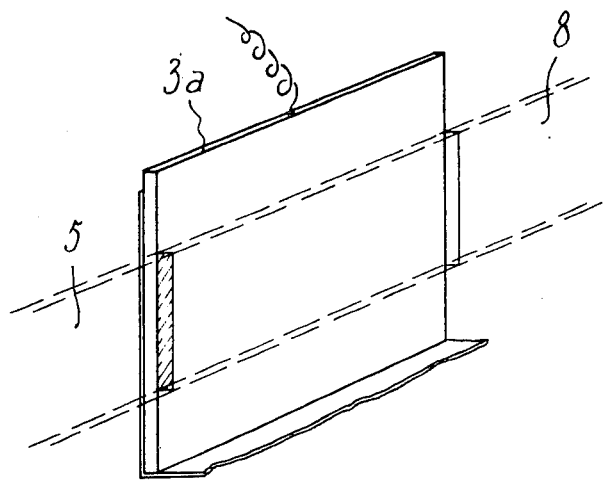
FIG. 2 is a partial view of the active electrode and of the beam of radiation.

The method according to this invention is based upon the discovery that it is possible to measure, in a D.C. electrical field and using a beam of radiation of suitable dimensions, the change in the number of colloidal particles in the space adjacent to one of the electrodes. It is necessary, in order to do this, to produce a beam, the thickness of which as viewed in the direction of the lines of force of the electrical field shall be less than $1,000\ \mu$, and preferably less than $500\ \mu$. The dimension in the direction perpendicular to the lines of force is not critical and depends solely upon practical considerations, such as for example the initial concentration of the solution, the turbidity and so on.

The best results are obtained if the beam passes through a zone, the side of which towards the electrode coincides with the surface of such electrode.

According to the invention use is made, for the measuring the mobility of the particles, of a tank of which two vertical opposed walls are transparent to the radiation used, while the other two walls may be formed of any material having the required sealing properties and sodility. Parallel to these two walls there is disposed a set of electrodes, intended for the creation of the electrical field in which is placed the colloidal solution or suspension which is to be subjected to measurement.

In practice, the shape of the tank will be so selected that the transparent walls are further apart than the other two vertical walls. The ratio of such wall spacing may be of the order of 1 to 5, but other ratios may be preferred, depending upon the colloids to be measured and the electrical fields to be applied.

The electrodes, which with advantage entirely cover the internal surface of the vertical walls which are not transparent, are spaced at a distance which in practice is of the order of 0.3 to 0.9 cm, but is is also possible that a lesser or greater distance may be preferred depending upon the particular case.

The electrodes are constructed of a material capable of adsorbing the electrochemical reaction prducts generated at the electrodes, in order not to disturb the electrophoresis, such as for example palladium.

In order to carry out the measuring of the global mobility of the colloidal particles according to this invention, the apparatus is equipped with a radiation source which is disposed in such a way that, by the use of a system of known type, a beam of radiation is produced parallel to the electrode in close proximity to which it is desired to carry out the measurement.

In the case of a luminous source, an optical system is used, comprising mirrors, lenses or slots.

It is also possible to carry out the measurements using infra-red radiation or gamma-radiation.

At the exit from the tank, the intensity of the beam is measured by means of a detector of known type for the radiation used.

Thus, in the case where a source of visible radiation is used, the detector is simply constituted of a cadmium sulphide photoresistor for example, the response of which is representative of the movement of the particles under the influence of the electrical field in a very short time, preferably less than 5 seconds. Any other method of measuring which is sensitive to the radiation issuing from the detection tank may be used.

By contrast with the known techniques for the determination of the mobility of the colloidal particles using electrophoresis, measurements are not made directly of the individual movements of a certain number of particles, but of the variation in the number of colloidal particles in a volume observed.

In fact, the particles form an obstacle to certain radiations, and cause an attenuation of such radiations when they pass through a thickness of colloidal suspension or solution.

According to the invention, the beam coming from the radiation source is directed essentially parallel to the electrodes. The volume of liquid observed is thus determined by the section of the beam and its length between the two transparent walls of the tank.

The presence of the colloids in the liquid weakens the beam of radiation, and this weakening is a function of the number of particles and will be indicated below and in the claims by the term "optical density".

The length of the beam, i.e. the length of the tank can vary in practice from 5 to 50 mm, and depends for a given intensity of the beam on the optical density of the solution or suspension to be measured.

A measurement is carried out of the mobility of the particles by the application of a D.C. electrical field between the electrodes, which causes a variation in the quantity of particles in the observed volume, and thus of the optical density, the consequence of which is a variation in the response of the detector. The greater the quantity of particles which move, the greater will be the variation in the optical density in a given interval of time.

In practice, electrical fields of 20 to 30 V/cm are sufficient for obtaining good results.

The measuring time, that is to say the time for the application of the electrical field, is less than 10 seconds and preferably ranges between 0 and 5 seconds.

The best reading results are obtained when the beam passes through the liquid in a zone situated in the vicinity of one of the two electrodes and does not exceed a thickness of 1,000 $\mu$, and preferably of 500 $\mu$, from the surface of such one electrode. The depth of the zone is not critical.

The electrode adjacent to which the measurement is carried out is called the active electrode. According to the charge of the particles, the polarity of the electrodes is selected in such a way that the particles move away under the effect of the electrical field from the active electrode.

In known manner, it is possible to calculate the average mobility of the particles and thus the electrokinetic potential.

A description is given below of a simple embodiment of the apparatus for carrying out this invention, by way of a non-limiting example.

The apparatus consists of an electrophoresis tank (1), the base of which measures 40 × 10 mm and the height of which is 40 mm. Against the lateral walls 2a, 2b, there are disposed two electrodes (3a, 3b), each measuring 40 × 50 mm and having a thickness of 2 mm, and formed of palladium plates. The tank makes possible a beam of radiation, the length of which between the walls which are transparent to the radiation is 40 mm. This length is sufficient for a liquid possessing a turbidity of 5-20 U.J.

For higher turbidity values, it is possible to reduce the length of the tank, for example to 10 mm.

A supply stabilised with transistors (4) regulates the intensity of the electrophoresis current. The active electrode (3a) is polarised either as a cathode, or as an anode, depending upon the polarity of the colloids, by means of an inverter switch, not shown. A measuring device for measuring the voltage at the terminals of the electrodes enables the electrical field used during the electrophoresis to be determined. The energy is supplied from a 12-volt battery, the capacity of which is associated with the period of utilisation. The active electrode (3a) is skimmed by a beam of light (5) issuing from the light source (6), comprising a straight filament lamp of four watts, through the intermediary of an optical system (7) comprising slots having a width of the order of 0.5 mm, and capable of transforming the diffuse radiation issuing from the light source into a unidirectional radiation beam.

The detecting of the luminous intensity of the emergent ray (8) is effected by a photoresistor cell (9) integrated into a wheat stone bridge and placed at the end of an optical cylindrical tube (10), the whole assembly constituting the detector cell being disposed opposite to the face at which the radiation emerges.

The variation in the concentration of the colloids in the vicinity of the active electrode 3a leads to a proportional deviation of the galvanometer needle (11).

A particularly useful application of the apparatus for carrying out this invention consists of measuring the optimum dose of coagulant to be introduced into a surface water to cause its clarification by performing a plurality of density change measuring operations.

In order to do this, 4 or 5 samples, for example, of the water to be clarified are prepared. To each sample is added an increasing quantity of a normally used coagulant, and the change in the optical density is measured according to this invention.

The reduction in the optical density observed dwindles with approach to the optimum quantity for which the colloid flocculates. After the "neutral" point has been passed, the optical density increases as soon as the electrical field is applied.

By way of example, a description is given below of the coagulation tests carried out using the apparatus described above.

The water was prepared by mixing 50 mg of kaolin with 1 liter of city main water. In order to determine the dose of coagulant to be added to this water in order to destabilise the suspension, the mobility of the colloidal particles was measured as a function of the concentration of the coagulant added, by subjecting the electrophoresis tank to an electrical field of 20 V/cm for 3 seconds.

The results are summarised in Table I.

Table I

| Concentration of added coagulant in ppm | 0 | 10 | 20 | 30 | 40 | 50 |
|---|---|---|---|---|---|---|
| Variation in optical density in arbitrary units | 10 | 6 | 4.5 | 1.5 | <0.5 | −5 |

For a coagulant dose of 40 ppm, the deviation of the galvonometer is practically zero; beyond 40 ppm, it becomes negative; from this it is deduced that the treatment dose is 40 ppm of coagulant.

Coagulation tests were carried out in the same manner for a river water. Under the same experimental conditions, the results listed in Table II below were obtained.

Table II

| Concentration of aluminium sulphate in ppm | 0 | 100 | 150 | 200 | 220 | 240 |
|---|---|---|---|---|---|---|
| Variation in optical density in arbitrary units | 85 | 33 | 25 | 4 | 0 | −10 |

The optimum dose of coagulating agent is therefore 220 ppm. The total analysis time was 5 minutes. The quantity of water required was 100 cm$^3$.

These tests show that the method is especially suitable for measurements on the spot, since the measuring times are short and the volumes required are small.

We claim:

1. A method for determining an optimum dosage of a coagulant to be added to a liquid to be treated and having colloidal particles suspended therein, to achieve optimum clarification of the liquid, said method comprising:

providing a tank having at two opposite walls thereof substantially parallelly spaced electrodes;

performing a plurality of density change measuring operations, each such density change measuring operation comprising:

placing a quantity of liquid to be treated within said tank;

adding a predetermined dosage of coagulant material to said liquid to thereby cause flocculation of colloidal particles within said liquid;

passing a flat beam of radiation completely longitudinally through said liquid in said tank at a position closely adjacent one of said electrodes and spaced from the other of said electrodes, while maintaining said beam of radiation parallel to said electrodes;

measuring the intensity of said beam of radiation after passage thereof through said tank to obtain a first measurement of optical density of said liquid;

thereafter applying an electric field between said electrodes, thereby causing the unflocculated of said colloidal particles to move from a first of said electrodes toward a second of said electrodes;

thereafter, after a predetermined period of time, again measuring the intensity of said beam of radiation after passage thereof through said tank to obtain a second measurement of optical density of said liquid, while maintaining said beam of radiation closely adjacent said first electrode; and comparing the first and second measurements of optical density to obtain a measurement of the change in optical density of the liquid as a function of the amount of unflocculated of said colloidal particles within said liquid;

the predetermined dosage of coagulant material added in each of said density change measuring operations being different; and comparing the measurements of change in optical density obtained from each of said density change measuring operations to determine the particular dosage representative of the least amount of change in optical density, such particular dosage representing the optimum dosage to achieve optimum clarification of the liquid to be treated.

2. A method as claimed in claim 1, wherein in each of said density change measuring operations said beam of radiation is maintained at a thickness of between 0 and 1,000$\mu$ as viewed in the direction of lines of force of said electric field from said first electrode to said second electrode.

3. A method as claimed in claim 2, wherein said thickness is between 0 and 500$\mu$.

4. A method as claimed in claim 1, wherein in each of said density change measuring operations said beam of radiation is directed through said tank at a position to just skim the interior surface of said first electrode.

5. A method as claimed in claim 1, wherein said radiation is visible light.

6. A method as claimed in claim 1, wherein said radiation is infra-red radiation.

7. A method as claimed in claim 1, wherein said radiation is gamma radiation.

8. A method as claimed in claim 1, wherein said electrodes are maintained at a relative spacing of from 0.3 to 0.9 cm.

9. A method as claimed in claim 1, wherein in each of said density change measuring operations the path of said beam of radiation, while passing through said liquid, has a length of from 5 to 50 mm.

10. A method as claimed in claim 1, wherein in each of said density change measuring operations an electric field of from 20 to 30 V/cm is applied.

11. A method as claimed in claim 1, wherein in each of said density change measuring operations said predetermined period of time is less than 10 seconds.

12. A method as claimed in claim 11, wherein in each of said density change measuring operations said predetermined period of time is between 0 and 5 seconds.

* * * * *